(12) United States Patent
Piasini et al.

(10) Patent No.: US 9,918,809 B2
(45) Date of Patent: Mar. 20, 2018

(54) DAMPENING INSERT FOR DENTAL IMPLANTS

(71) Applicant: KULZER GMBH, Hanau (DE)

(72) Inventors: Bruno Piasini, Sondrio (IT); Antonio Maria Scotti, Monza e Brianza (IT)

(73) Assignee: Kulzer GmbH, Hanau (DE)

( * ) Notice: Subject to any disclaimer, the term of this patent is extended or adjusted under 35 U.S.C. 154(b) by 0 days.

(21) Appl. No.: 15/107,446

(22) PCT Filed: Jan. 16, 2015

(86) PCT No.: PCT/EP2015/000098
§ 371 (c)(1),
(2) Date: Jun. 22, 2016

(87) PCT Pub. No.: WO2015/120954
PCT Pub. Date: Aug. 20, 2015

(65) Prior Publication Data
US 2016/0338802 A1    Nov. 24, 2016

(30) Foreign Application Priority Data
Feb. 11, 2014 (EP) .................................... 14154628

(51) Int. Cl.
*A61C 8/00* (2006.01)
(52) U.S. Cl.
CPC .......... *A61C 8/0086* (2013.01); *A61C 8/0016* (2013.01); *A61C 8/0068* (2013.01)

(58) Field of Classification Search
CPC .... A61C 8/0086; A61C 8/0016; A61C 8/0068
See application file for complete search history.

(56) References Cited

U.S. PATENT DOCUMENTS

| 3,827,145 | A | * | 8/1974 | Richards | A61C 13/30 433/175 |
| 4,324,550 | A | * | 4/1982 | Reuther | A61C 8/0022 433/169 |
| 4,416,629 | A | * | 11/1983 | Mozsary | A61C 8/0022 433/173 |

(Continued)

FOREIGN PATENT DOCUMENTS

DE    8905201    9/1989
EP    0370590    5/1990

*Primary Examiner* — Cris L Rodriguez
*Assistant Examiner* — Hao D Mai
(74) *Attorney, Agent, or Firm* — Themis Law (57) ABSTRACT

An insert for a dental prosthesis screwed onto an implant, in particular of the type having a superstructure and an implant to be integrated in the bone, which are reciprocally joined by a screw. The insert is composed of an element made of a damping material interposed between the coupling surface of the superstructure and the implant. With an insert according to the invention, a dental prosthesis screwed onto an implant is obtained, which reproduces the natural anchoring state of the tooth to the bone, so that the stress peaks on the superstructure are damped before being discharged onto the implant and consequently also onto the bone. An insert according to the invention also offers the advantage of sealing the contact area between the superstructure and the implant, thus preventing dangerous bacterial infiltrations.

4 Claims, 7 Drawing Sheets

(56) References Cited

U.S. PATENT DOCUMENTS

| | | | | |
|---|---|---|---|---|
| 4,447,210 A * | 5/1984 | Hidaka | A61C 8/0086 | 433/169 |
| 4,552,532 A * | 11/1985 | Mozsary | A61C 8/0086 | 433/173 |
| 4,631,031 A * | 12/1986 | Richter | A61C 8/0018 | 433/173 |
| 4,731,085 A * | 3/1988 | Koch | A61C 8/0018 | 433/173 |
| 4,780,080 A * | 10/1988 | Haris | A61C 8/0022 | 433/173 |
| 4,793,808 A * | 12/1988 | Kirsch | A61C 8/0018 | 433/173 |
| 4,842,518 A * | 6/1989 | Linkow | A61C 8/0018 | 433/174 |
| 4,881,897 A * | 11/1989 | Franek | A61C 8/0018 | 433/169 |
| 4,950,161 A * | 8/1990 | Richter | A61C 8/005 | 433/169 |
| 4,993,950 A | 2/1991 | Mensor, Jr. | | |
| 5,026,280 A * | 6/1991 | Durr | A61C 8/0086 | 433/173 |
| 5,040,982 A * | 8/1991 | Stefan-Dogar | A61C 8/005 | 433/169 |
| 5,052,931 A * | 10/1991 | Kirsch | A61C 8/0018 | 433/173 |
| 5,061,285 A * | 10/1991 | Koch | A61C 8/0018 | 433/173 |
| 5,073,111 A * | 12/1991 | Daftary | A61C 8/005 | 433/173 |
| 5,527,182 A * | 6/1996 | Willoughby | A61C 8/0001 | 433/172 |
| 5,954,505 A * | 9/1999 | Ford | A61C 8/0086 | 433/173 |
| 6,497,573 B2 * | 12/2002 | Wagner | A61C 8/005 | 433/173 |
| 7,850,452 B2 * | 12/2010 | Suttin | A61C 8/0022 | 433/173 |
| 2009/0240336 A1 * | 9/2009 | Vander Meulen | A61F 2/3804 | 623/18.11 |
| 2015/0111178 A1 * | 4/2015 | Lin | A61C 8/0018 | 433/201.1 |
| 2015/0147724 A1 * | 5/2015 | Staudenmann | A61C 8/0059 | 433/201.1 |
| 2015/0313694 A1 * | 11/2015 | Piasini | A61C 13/26 | 433/173 |

* cited by examiner

DAMPENING INSERT FOR DENTAL IMPLANTS

The present invention relates to an insert, in particular having a cushioning effect, for a dental prosthesis screwed onto an implant. The invention also relates to the dental prosthesis provided with this insert.

FIELD OF THE INVENTION

The field of invention relates to dental prostheses screwed onto an implant, in which a superstructure is fixed, by means of a screw, onto the implant integrated in the bone.

BACKGROUND OF THE INVENTION

The fixing of a superstructure onto an implant is traditionally effected by direct contact between the parts, i.e. without any intermediate elements suitable for separating the respective contact surfaces. Any stress on the superstructure, generated in particular by mastication, is consequently discharged directly onto the implant and therefore also onto the bone sustaining it. The stress peaks transmitted onto the contact surface between the bone and the implant are, however, particularly detrimental as they can cause the detachment of the implant from its seat and consequently instability of the prosthesis, with a possible loss of the implant.

SUMMARY OF THE INVENTION

An objective of the present invention is to provide a dental prosthesis which is similar to the natural state of the tooth, in which the stress peaks are damped before being discharged onto the bone.

A further objective of the present invention is to provide a prosthesis suitable for preventing the stress peaks received by the superstructures from reaching the bone unaltered.

Another objective of the invention is to provide a prosthesis suitable for preventing infiltrations of bacteria between the surfaces in reciprocal contact, of the implant and superstructure, respectively.

Yet another objective of the invention to protect the surface of the dental superstructure in contact with the implant, thus avoiding possible damage due to the reciprocal fixing operations between these parts, and movements caused by mastication.

These and other objectives are achieved by means of the insert and prosthesis of claims 1 and 9 respectively. Some preferred embodiments of the invention are described in the remaining claims.

In particular, the insert of the invention, comprises a superstructure and an implant integrated in the bone, which are reciprocally joined by means of a screw, wherein said insert consists of an element made of -a damping material interposed between the coupling surfaces of the superstructure and implant, respectively.

According to the invention, said insert consists of an element having an annular shape provided with a hole for the passage of the above-mentioned screw.

In particular, the insert of the invention consists of an element containing a base suitable for being interposed between the above-mentioned coupling surfaces, said insert also having a profile which is engaged with the coupling section between the superstructure and the implant.

The insert of the invention is also characterized in that it consists of an element having an annular base suitable for being interposed between the above-mentioned coupling surfaces of the superstructure and implant, a profile which is engaged inside said superstructure and a threaded portion to be engaged with a cap, also threaded, for blocking, said superstructure on the insert, said screw causing the fixing of the insert on the implant.

According to a variant, the insert of the invention consists of an element having an annular base suitable for being interposed between the above-mentioned coupling surfaces and a profile which is engaged inside said above-mentioned superstructure, said screw having a conical portion which, when engaged inside the hole of the insert, causes the expansion of said profile, thus blocking the superstructure on the insert and on the implant.

The insert of the invention is also characterized in that it comprises a protrusion suitable for being engaged with a corresponding housing of the superstructure, thus blocking its rotation on the same insert.

The latter is particularly made of an elastically deformable plastic material which, when subjected to a preload of 10-50 Nm by means of said screw 5, in the presence of additional loads as those performed by the masticatory apparatus, undergoes an elastic deformation of 0.01-80 $\mu$ (micron) in the direction of the vertical axis.

Thanks to the insert of the invention, a dental prosthesis is obtained, which is screwed onto an implant which reproduces the natural anchoring state of the tooth to the bone, so that the stress peaks on the superstructure are damped before being discharged onto the implant and consequently also onto the bone.

The insert of the invention also offers the advantage of sealing the contact area between the superstructure and implant, thus preventing any dangerous infiltrations of bacteria.

Again, thanks to the cushioning effect generated by the insert of the invention, made of a material suitable for the purpose, damage to the superstructure is prevented, due to contact of the same with the implant during the fixing operations between the parts and also during mastication.

BRIEF DESCRIPTION OF THE DRAWINGS

These and other objectives, advantages and characteristics are evident from the following description of some preferred embodiments of the insert and prosthesis of the invention, illustrated, as a non-limiting example, in the figures of the enclosed drawings. In which.

DETAILED DESCRIPTION OF THE DRAWINGS

Figure 1:
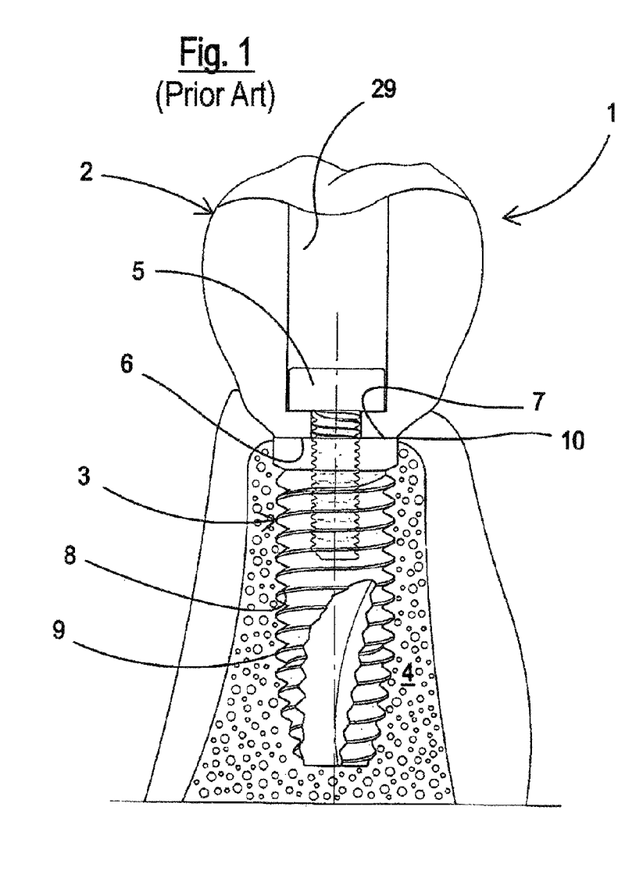
FIG. 1 illustrates a sectional view of a dental prosthesis screwed according to the known art.

The prosthesis of the known art illustrated in FIG. 1, indicated as a whole with 1, consists of a superstructure 2 fixed on the implant 3 anchored to the bone 4, by means of a screw 5, housed inside the hole of the same superstructure 2. In this embodiment, the surface 6 of the superstructure and the surface 7 of the implant are in direct contact with each other at the interface between the superstructure 2 and the implant 3. The stress peaks on the superstructure are therefore discharged directly, first onto the side surface 9 of the implant 3 and from there onto the surface 8 of the bone 4. As a result, the mentioned surfaces 8 and 9 can be reciprocally detached, thus causing a loss in the hold of the implant in its seat and requiring the re-establishment or re-implantation of the implant itself.

From FIG. 1, it can also be observed that, at the interface of the mentioned surfaces 6 of the superstructure 2 and 7 of the implant 3, there are inevitably interspaces 10, normally due to the mechanical production tolerances of these parts. These interspaces have the disadvantage of representing seats for undesired and dangerous bacterial proliferation.

For the same reasons, the same surfaces 6 and 7, in direct contact with each other, can be damaged by the stress of mastication.

Figure 2:
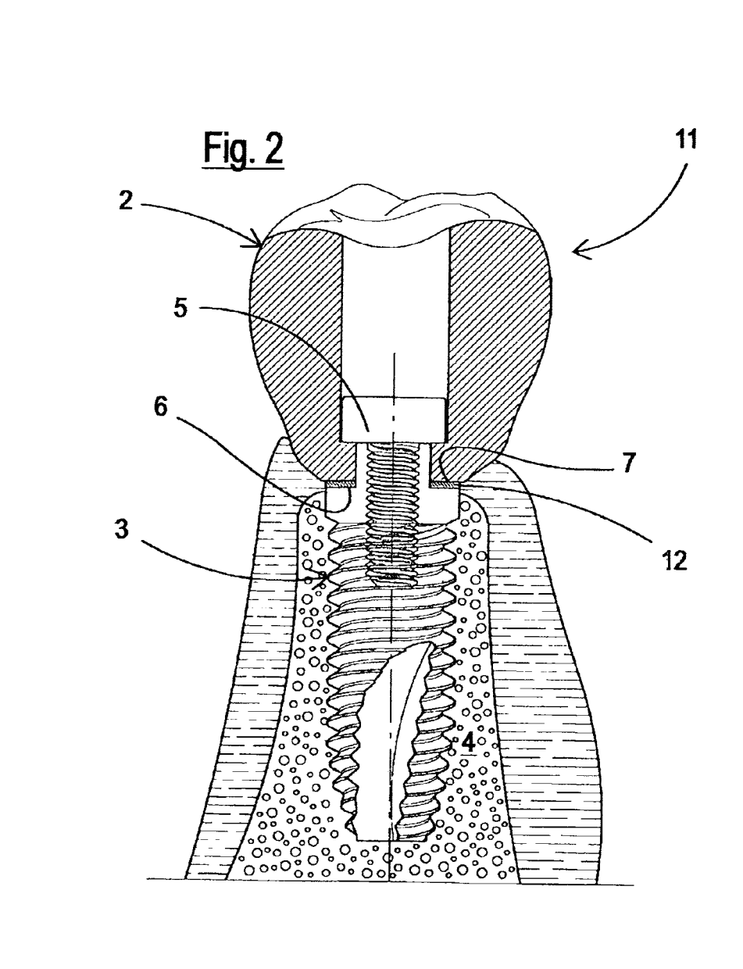
FIG. 2 illustrates a sectional view of a first embodiment of the dental prosthesis screwed according to the invention.

All of these drawbacks are solved by means of the prosthesis 11 of FIG. 2, in which an insert 12 is interposed between the facing surfaces 6 of the superstructure 2 and 7 of the implant 3. As better illustrated in FIGS. 3 and 4, this insert 12 substantially consists of a circular washer, having a central hole 13 for the passage of the screw 5 which blocks the superstructure 2 to the implant 3.

Figure 3:
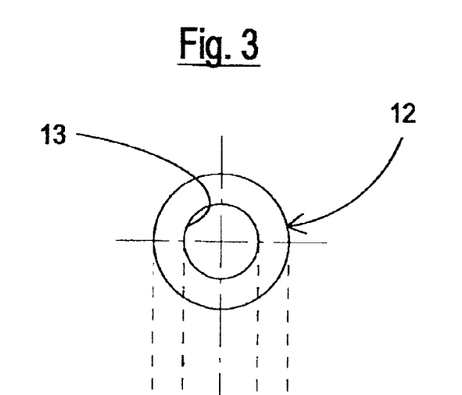
FIGS. 3 and 4 illustrate a plan and sectional view, respectively, of the insert assembled on the prosthesis of FIG. 2.
Figure 4:
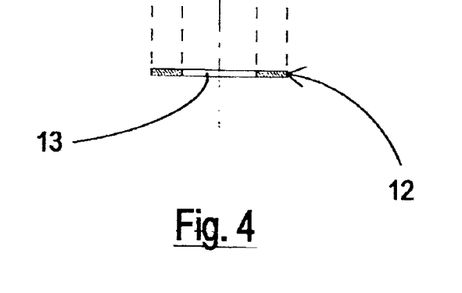
Figure 5:
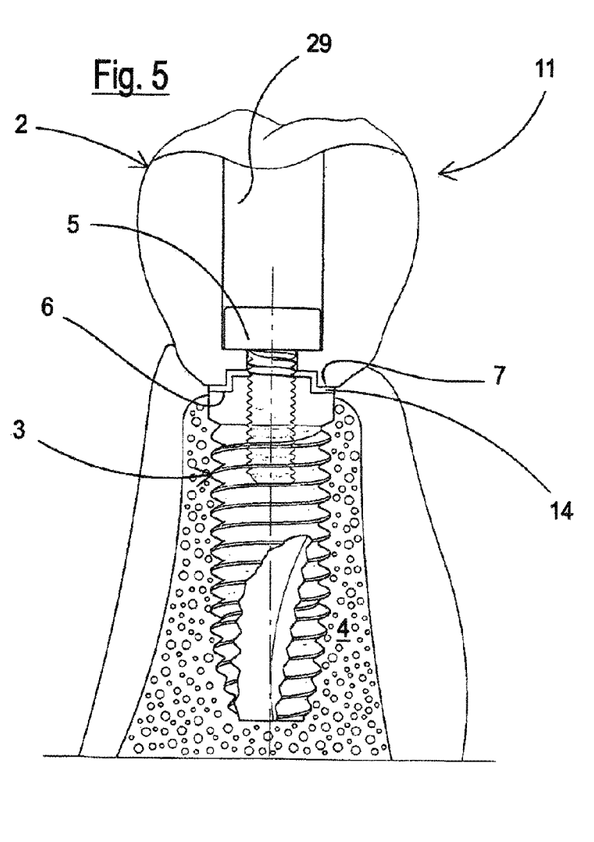
FIG. 5 illustrates a variant of the prosthesis and insert of FIGS. 2 to 4.
Figure 6:
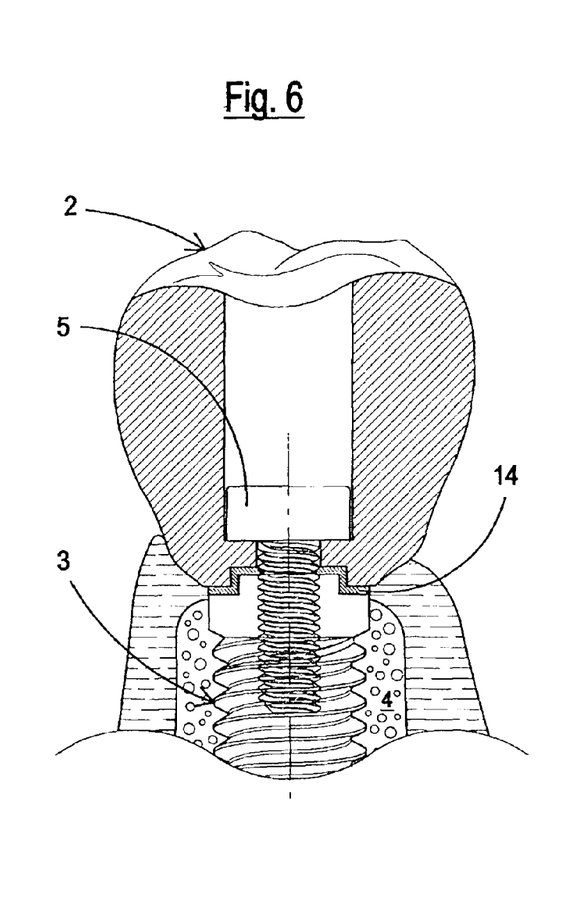
FIG. 6 illustrates a detail of an anchorage for an implant having an external connection with the insert positioned between the superstructure and the implant of the prosthesis of FIG. 5.

As a result of its damping and protective cushioning functions between the surfaces 6 of the superstructure 2 and 7 of implant 3, the material of the insert 12 must be less rigid than those forming the superstructure (for example ceramic, titanium and chromium/cobalt alloys) and those used for the production of the implant (for example titanium).

The formation material of the insert 12 is preferably an elastically deformable plastic material which, when subjected to a preload of 10-50 Nm by means of said screw 5, in the presence of additional loads as those exercised by the masticatory apparatus (generally up to 400 N), undergoes an elastic deformation of 0.01-80 μ (micron) in the direction of the vertical axis. To this purpose the material forming the insert 12 must exhibit an elastic modulus sufficient to restore its initial geometry in the absence of the masticatory load.

Figure 7:
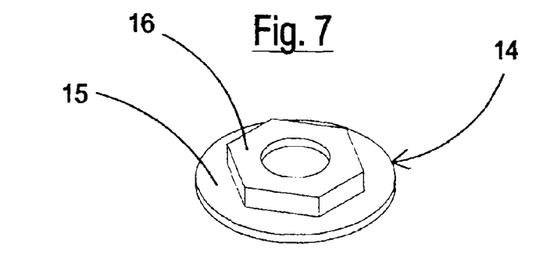
FIGS. 7, 7a and 8 illustrate a perspective, plan and sectional view, respectively, of the insert assembled on the prosthesis of FIG. 6.
Figures 7A, 8:
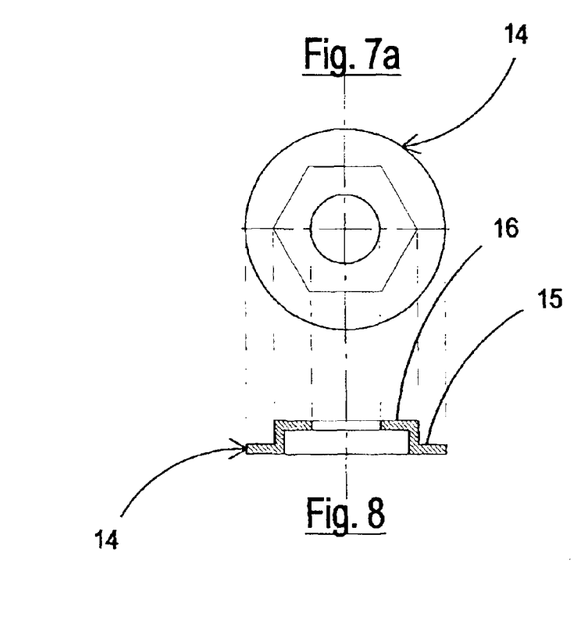
Figure 9:
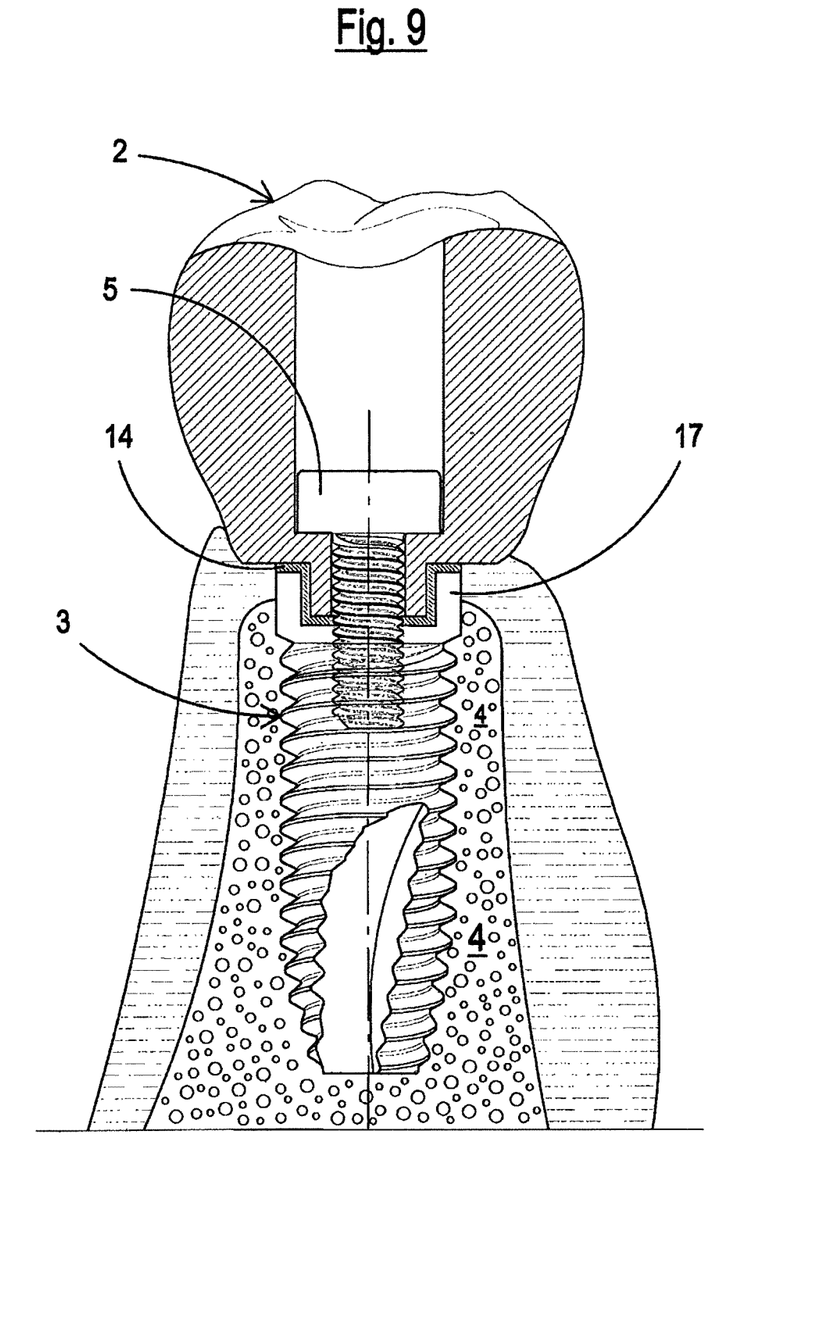
FIG. 9 illustrates a detail of an anchorage for an implant having an internal connection, between the superstructure and the implant of the prosthesis of the invention.

In the embodiment of FIGS. 5 to 8, the insert 14 has an annular base 15 in a single piece, with a profile 16 which reproduces the form of the coupling section between the superstructure 2 and the implant 3. In this variant, the annular base 15 of the insert 14 has the protective cushioning and damping functions already described with reference, to the washer 12 of FIGS. 3 and 4, whereas the profile 16 acts as a damping and centering component between the implant 3 and the superstructure 2. As illustrated in FIG. 7, the outer section of the profile 16 of the insert 14, advantageously has the form of the corresponding coupling section of the implant, thus also obtaining an anti-rotational effect. As illustrated in FIG. 9, the insert 14 is positioned at the side of the inner connection 17 of the implant, and no longer externally such as that represented in FIG. 6.

Figure 10:
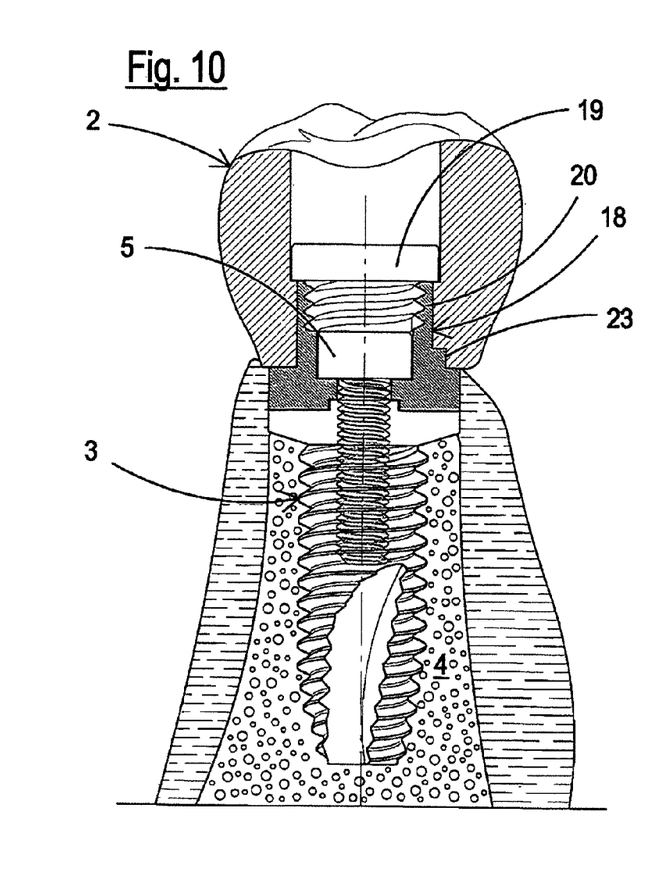
FIG. 10 illustrates a sectional view of a second embodiment of a screwed dental prosthesis of the invention, with an insert having a floating anchorage and retention cap of the superstructure.
Figure 11:
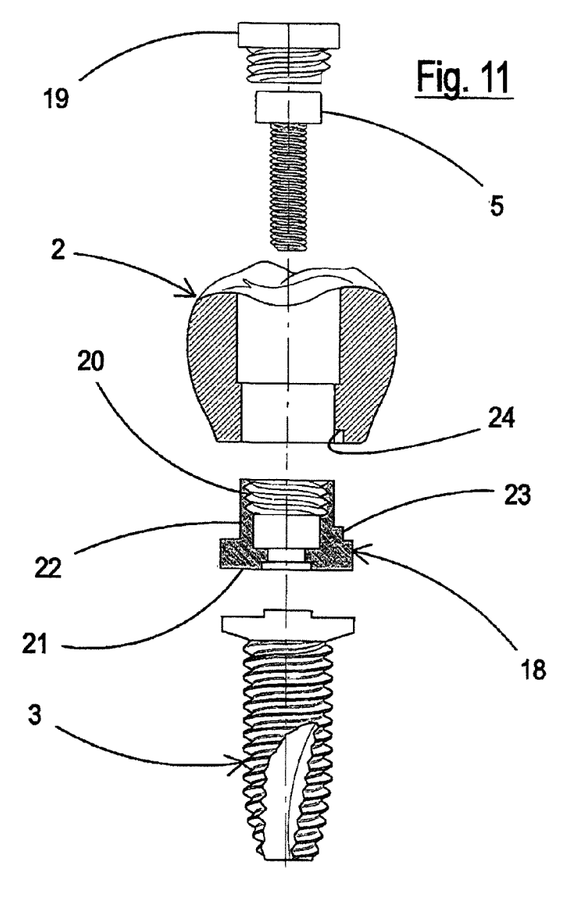
FIG. 11 illustrates an exploded view of the prosthesis of FIG. 10.
Figure 14:
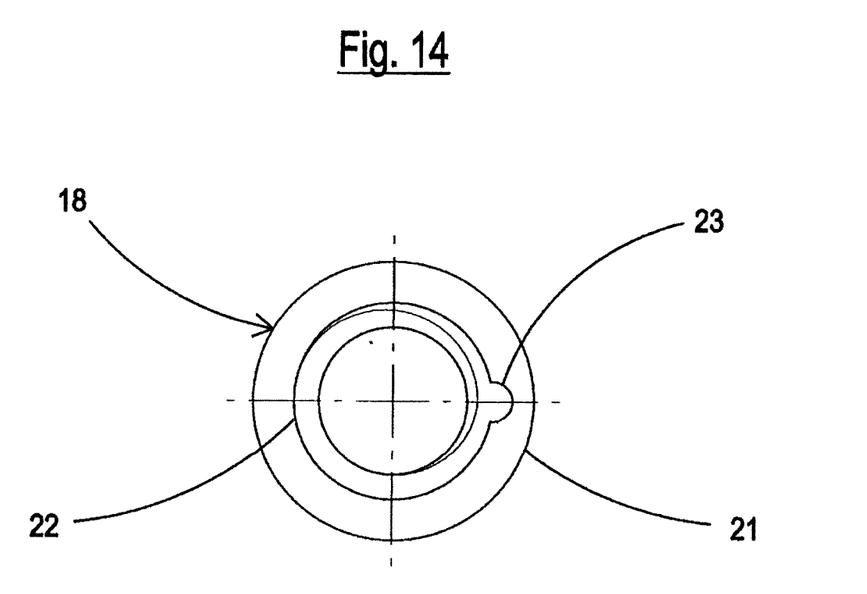
FIG. 14 illustrates a plan view of the insert of the prosthesis of FIGS. 10 to 13.

Unlike the prosthesis of FIGS. 2 to 5, in which the screw 5 is used for reciprocally fixing the superstructure, implant and insert, in the variant of FIGS. 10 and 11, the screw 5 joins the insert 18 to the implant 3, whereas, for the anchorage of the superstructure 2 to the insert 18 (and therefore also to the implant 3), a threaded cap 19 is used, which is screwed onto the corresponding threaded portion 20 of the insert 18. In this variant, as is better illustrated in FIG. 11, the insert 18 has an annular base 21, a profile 22 with the described threaded portion 20, and is also produced with the same material used for the inserts 12 and 14 previously described. The insert 18 of FIG. 14 advantageously has a protrusion 23 which, by engagement in a corresponding housing 24 inside the superstructure 2 of FIG. 11, has an anti-rotational function between the same structure and the insert.

Figure 12:
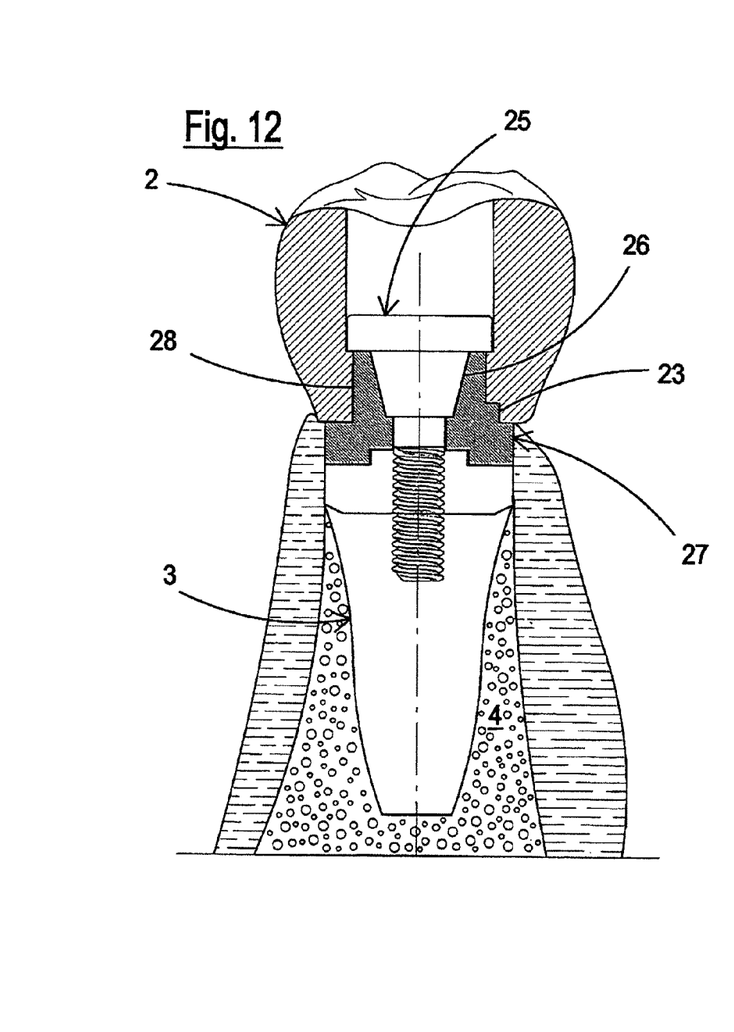
FIG. 12 illustrates a sectional view of a third embodiment of a screwed dental prosthesis according to the invention, with an insert having a floating anchorage and with retention of the superstructure with a conical coupling.
Figure 13:
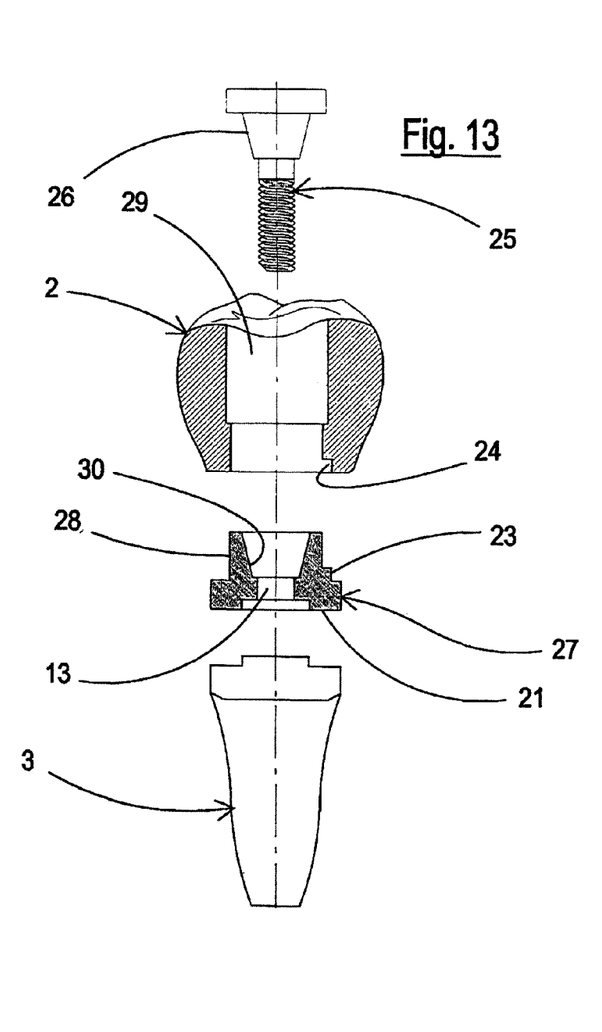
FIG. 13 illustrates an exploded view of the prosthesis of FIG. 12.

In the variant of FIGS. 12 and 13, a screw 25 is used for the reciprocal anchorage between the superstructure 2, the insert 27 and the implant 3, said screw having a conical portion 26, in turn suitable for being engaged inside the base 30, also having a corresponding conical form, of the hole 13 of the insert 27. Therefore, when the screw 25 is engaged inside the hole 13 of the insert 27, its profile 26 compresses the base 30 of the hole 13, thus expanding the outer profile 28 of the insert 27 against the corresponding inner surface of the hole 29 of the superstructure 2, thus blocking the superstructure without the necessity of the cap 19 of the version of FIG. 11.

Having thus described some preferred exemplary embodiments of the device of the present invention in accordance with the principles of the present invention, it should be apparent to those skilled in the art that various additional objects and advantages have been attained by the invention and that a variety of modifications can be made within the scope of the present invention, being limited by the following appended claims only.

The invention claimed is:

1. A dental prosthesis comprising:
a superstructure;
an implant adapted to be integrated into a bone;
a screw coupling the superstructure to the implant; an insert made of a damping material, adapted to be disposed between the superstructure and the implant,
wherein the superstructure has a cavity facing the implant, and the implant has a protuberance facing the cavity,
wherein the insert comprises an outer annular portion and an inner protruding portion which extends longitudinally from the outer annular portion,
wherein the inner protruding portion and the outer annular portion have a central opening for passage of the screw,
wherein the inner protruding portion is dimensioned to be received in the cavity, and
wherein the outer annular portion extends to an outer edge of a side of the implant facing the superstructure and has a second cavity which is longitudinally aligned with the central opening and which receives the protuberance; and a threaded cap, wherein the inner protruding portion of the insert has an inner threaded portion that receives at least part of the threaded cap, so as to provide a cover for a head of the screw after the screw is disposed through the central opening and engages the implant.

2. The dental prosthesis according to claim 1, wherein the insert comprises a protrusion extending from a lateral wall of the insert, the protrusion engaging a mating housing in the cavity to prevent a relative rotation between the insert and the superstructure.

3. The dental prosthesis according to claim 1, wherein the insert is made of an elastically deformable plastic material which, when the insert is subjected to a preload of 10-50 Nm by the screw, or in presence of loads provided by a masticatory apparatus, undergoes a longitudinal elastic deformation.

4. The dental prosthesis according to claim 3, wherein the longitudinal elastic deformation of the elastically deformable plastic material is 0.01 to 80 μ (micron).

* * * * *